United States Patent [19]
Grüning et al.

[11] Patent Number: 5,391,321
[45] Date of Patent: Feb. 21, 1995

[54] LIQUID OR PASTY, STORAGE-STABLE MULTIPLE EMULSIONS OF THE $O^1/W/O^2$ TYPE

[75] Inventors: Burghard Grüning; Peter Hameyer; Christian Weitemeyer, all of Essen, Germany

[73] Assignee: Th. Goldschmidt AG, Essen, Germany

[21] Appl. No.: 21,718

[22] Filed: Feb. 24, 1993

[30] Foreign Application Priority Data

Mar. 4, 1992 [DE] Germany ............... 4206732

[51] Int. Cl.$^6$ ............... B01F 17/34; B01J 13/00
[52] U.S. Cl. ............... 252/309; 252/312; 252/356; 252/DIG. 1; 514/941; 514/943
[58] Field of Search ........ 252/309, 312, 356, DIG. 1; 514/941, 943; 44/301; 424/78.03

[56] References Cited

U.S. PATENT DOCUMENTS

| | | | |
|---|---|---|---|
| Re. 21,322 | 1/1940 | Harris ............... | 252/356 X |
| 4,254,105 | 3/1981 | Fukuda ............... | 514/943 X |
| 4,532,132 | 7/1985 | Keil ............... | 514/772 |
| 4,590,086 | 5/1986 | Takahashi et al. ............... | 252/312 X |
| 4,675,179 | 6/1987 | Suzuki et al. ............... | 514/941 X |
| 4,698,178 | 10/1987 | Hüttinger et al. ............... | 252/309 |
| 4,857,506 | 8/1989 | Tyle ............... | 514/937 X |
| 4,985,250 | 1/1991 | Bee et al. ............... | 514/943 X |
| 5,133,898 | 7/1992 | Fock et al. ............... | 252/356 |

FOREIGN PATENT DOCUMENTS

| | | |
|---|---|---|
| 0391124 | 10/1990 | European Pat. Off. . |
| 0459705 | 12/1991 | European Pat. Off. . |
| 3906702 | 9/1990 | Germany . |

OTHER PUBLICATIONS

*McCutcheon's Detergents & Emulsifiers*, 1973 No. American Edition, Publ. By McCutchen's Div., Allured Publ. Corp., Ridgewood, N.J. (1973), pp. 83 & 208.

*Primary Examiner*—Richard D. Lovering
*Attorney, Agent, or Firm*—Anderson Kill Olick & Oshinsky

[57] ABSTRACT

A liquid or pasty, storage-stable, multiple emulsion of the $O^1/W/O^2$ type, in which $O^2$ forms an outer phase of the multiple emulsion, a hydrophilic emulsifier being present at the $O^1/W$ interface and a hydrophobic emulsifier being present at the $W/O^2$ interface, is prepared where
(1) the hydrophobic emulsifier has an HLB value of at most 8 and
   a$_1$) a polyacrylate ester with long-chain hydrocarbon and polyoxyalkylene groups, or
   a$_2$) a polyoxyalkylenepolysiloxane with long-chain alkyl groups linked to silicon atoms, and
(2) the hydrophilic emulsifier is a nonionic emulsifier with an HLB value of more than 8.

5 Claims, No Drawings

LIQUID OR PASTY, STORAGE-STABLE MULTIPLE EMULSIONS OF THE $O^1/W/O^2$ TYPE

FIELD OF THE INVENTION

The invention relates to a liquid or pasty, storage-stable, multiple emulsion of the $O^1/W/O^2$ type, in which $O^2$ forms the outer phase of the multiple emulsion, a hydrophilic emulsifier being present at the $O^1$ interface and a hydrophobic emulsifier being present at the $W/O^2$ interface.

BACKGROUND INFORMATION AND PRIOR ART

Multiple emulsions of the O/W/O type have gained in importance, particularly in cosmetics and also in some industrial applications. For example, multiple emulsions are used when two or more oil-soluble substances are to be present separated from one another in the emulsions in order to avoid their interactions with one another or if a substance is dissolved in the inner, oily phase, which is to be protected, for example, from the oxygen of the air.

Cosmetic preparations of this type are described in the European patent application 0 391 124. The patent application is directed to an emulsion, which is obtained by first converting an oily phase, which contains 1 to 30% by weight (based on the total preparation) of a fat, which is a solid at 25° C., and 0.01 to 5% by weight of a hydrophilic emulsifier, with water, which contains a water-soluble humectant, into an O/W emulsion and then mixing this O/W emulsion with a second oil phase, which represents the continuous, outer phase. This outer phase constitutes 10 to 70% by weight and is an oil, which is liquid at 25° C. and contains 0.5 to 10% by weight of a hydrophobic emulsifier. This multiple emulsion, described in the European patent application 0 391 124, thus contains an oil component, which is a solid at room temperature, in the inner phase. By these means, a certain stability of the emulsion is attained as well as demixing and/or interactions of the emulsifiers with one another, which would cause instability of the emulsion, are prevented.

OBJECT OF THE INVENTION

An object of the present invention is multiple emulsions of the $O^1/W/O^2$ type, the inner, oily $O^1$ phase of which is a liquid. Despite this inner, oily phase, the multiple emulsions have a high storage stability. The concept of storage stability means that no changes in the distribution state of an emulsion can be recognized during a storage time of three months at room temperature and at 40° C.

SUMMARY OF THE INVENTION

The present invention describes liquid or pasty, storage-stable, multiple emulsions of the $O^1/W/O^2$ type, in which $O^2$ forms the outer phase of the multiple emulsion, a hydrophilic emulsifier is present at the $O^1/W$ interface and a hydrophobic emulsifier is present at the $W/O^2$ interface, are obtained if, in a characteristic inventive manner, (1) the hydrophobic emulsifier has an HLB value of at most 8 and is $a_1$) a polyacrylate ester with long-chain hydrocarbon and polyoxyalkylene groups, or $a_2$) a polyoxyalkylenepolysiloxane with long-chain alkyl groups linked to silicon atoms, and (2) the hydrophilic emulsifier is a nonionic emulsifier with an HLB value of more than 8.

In accordance with the present invention, the HLB value is to be regarded as comparison value, which is determined experimentally. It is described in greater detail, for example, in the paper by W. C. Griffin, "Classification of surface-active agents by HLB," *J. Soc. Cosmetic Chemists*, 1,311 (1950).

The Hydrophobic Emulsifier

The hydrophobic emulsifier is characterized initially by its HLB value. It should not be greater than 8 and preferably not greater than 6. Pursuant to the invention, the hydrophobic emulsifier is selected from two groups of polymeric compounds:

$a_1$) polyacrylate esters with long-chain hydrocarbon and polyoxyalkylene groups, $a_2$) polyoxyalkylene polysiloxanes with long-chain alkyl groups linked to silicon atoms.

The hydrophobic emulsifiers of group $a_1$) are described in the German patent 39 06 702. They may be obtained by the transesterification of alkyl polyacrylates, which are obtained by free radical polymerization and the alkyl groups of which have 1 to 4 carbon atoms, with a mixture of a) alcohols, selected from the group consisting of
  a1 saturated aliphatic alcohols with 4 to 22 carbon atoms,
  a2 unsaturated aliphatic alcohols with 8 to 22 carbon atoms,
  a3 alkylphenols, the alkyl groups of which in each case have 8 to 12 carbon atoms, or their oxyalkylation products with 1 to 3 oxyethylene and/or oxypropylene units and b) polyoxyalkylene monools of the general, average formula $$R^1O-(C_nH_{2n}O-)_xH \qquad (I)$$

wherein
  $R^1$ is the hydrocarbon group of an $R^1OH$ starter alcohol
  n is 2, 3 or 4 and has an average value of 2 to 3 in the average polyoxyalkylene group
  x has an average value of 4 to 50 in the average polyoxyalkylene group, the molar ratio of a:b and the value of the subscripts n and x being selected so that the product has an HLB value of, at most, 8, in such amounts that up to 70% of the ester groups are transesterified, in the presence of a known transesterification catalyst at temperatures of 70° to 160° C., optionally in the presence of a solvent.

It is clear to those skilled in the art that the HLB value of the polyacrylate ester also depends on the chain length of the alcohol a).

The hydrophobic emulsifiers of group $a_2$) are known from U.S. Pat. Nos. 4,532,132 and 4,698,178. They are predominantly linear siloxanes, which have lateral and/or terminal long-chain alkyl groups as well as polyether groups. The HLB values of these compounds is determined by the hydrophilicity of the polyether group or groups, the chain length of the siloxane and the chain length of the long-chain alkyl group. The modified polysiloxanes can correspond to the following formula:

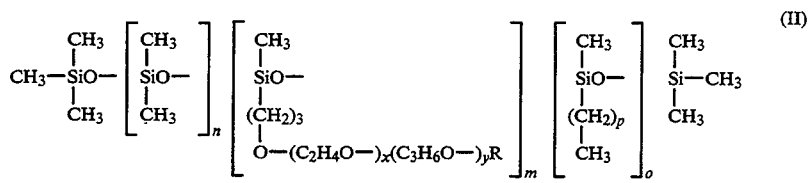

wherein
R is a lower molecular weight alkyl group or a hydrogen group
n is 10 to 200
m is 1 to 25
o is 1 to 100
p is 7 to 17 and
x and y are whole numbers from 1 to 200.

The hydrocarbon chain of the long-chain group can be interrupted by an ether oxygen. Such compounds are described in the EP-A-O 459 705.

The hydrophilic emulsifier, present at the $O^1/W$ interface, should be nonionic and have an HLB value of more than 8 and preferably of more than 12. Suitable nonionic emulsifiers are polyoxyethylene ethers of fatty alcohols, partial fatty acid esters and alkylphenols or polyoxyethylene esters of fatty acids.

A preferred nonionic emulsifier is the polyoxyethylene ester of ricinoleic acid.

Further, preferred hydrophilic nonionic emulsifiers are
b₁) the partial fatty acid esters of monoglycerin, oligoglycerin or polyglycerin or
b₂) the polyacrylate esters with long-chain hydrocarbon groups and polyoxyalkylene groups.

The hydrophilic emulsifiers of the b₁) type are monoesters or monoesters/diesters of glycerin or partial esters, particularly of di-, tri-, tetra- or pentaglycerin.

A partially monofatty acid ester of triglycerin corresponds to the example of formula

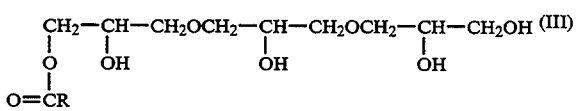

in which the

is the acyl group of a R—COOH fatty acid.

As fatty acids, particularly the saturated fatty acids with a chain length of 12 to 18 carbon atoms are utilized.

To adjust the HLB of the hydrophilic emulsifier b₁) to the desired value, ethylene oxide can be added in an appropriate amount to one or several OH groups of the partial fatty acid esters of the mono-, oligo- or polyglycerin in an addition reaction.

If fatty acid mono- or mono/diesters of glycerin are used, the HLB value of these materials can be increased by the addition of alkali salts of fatty acids with 10 to 18 carbon atoms. Such soap-containing partial esters of glycerin and fatty acids are self emulsifying.

The hydrophilic emulsifier b₂) corresponds structurally to the already described hydrophobic emulsifier a₁); however, it has a higher content of oxyethylene groups in order to bring about the required HLB value of more than 8. The HLB value is furthermore affected by varying the chain length of the siloxane and/or of the long-chain hydrocarbon groups.

The hydrophilic and the hydrophobic emulsifiers are added in amounts of 0.5 to 5% by weight, based on the total preparation.

The multiple emulsions are prepared by known procedures. To begin with, the inner phase of the multiple emulsion, that is, the emulsion of the $O^1/W$ type, is prepared by dissolving the hydrophilic emulsifier in the water phase and stirring the oil into the aqueous phase. It is, however, also possible to disperse the emulsifier in the oily phase and to stir the water into this phase. The $O^1/W$ emulsion obtained can optionally be homogenized by the action of shear forces. In a second step, the hydrophobic emulsifier is dispersed in the $O^2$ oily phase. The $O^1/W$ emulsion is then incorporated into this dispersion.

The active ingredients, such as vitamins, plant and organ extracts, fragrances, pharmaceutically active substances, etc. are dissolved or dispersed in the desired phase before the emulsification.

The inventive, multiple emulsions are liquid to pasty. They are stable when stored for several months and are therefore merchantable. The heat stability of the inventive emulsions is of particular advantage.

In the following examples, the formulation and preparation of inventive O/W/O emulsions are described, it being understood that the examples are given by way of illustration and not by way of limitation.

In addition, comparison emulsions are shown, which contain proven, but not inventive emulsifiers and therefore are inadequately stable.

The formation of the ternary emulsion form can be confirmed indirectly by comparison with reference samples, which have a binary character due to the method utilized to produce them. Appropriate emulsions are also called upon for comparison.

1. Basic Composition of the Inventive and Noninventive Emulsions 1.1 Composition of the Binary Comparison Emulsions Binary Comparison Emulsion I These are binary W/O emulsions, the outer oil phase of which ($O^2$) has the same composition and the same proportions by weight as that of the multiple emulsions and the inner phase of which contains only water instead of the O/W emulsion ($O^1/W$) of the multiple emulsions. The ternary emulsion and the binary comparison emulsion must have approximately the same viscosity, since essentially the concentration by weight and the viscosity of the outer oil phase ($O^2$) are responsible for this.

Binary Comparison Emulsion II

These are binary W/O emulsions, the composition of which, as percentages, is identical with that of the ternary emulsion, but in which all the lipid-like components ($O^1$ and $O^2$) are contained in the outer phase. As a result, the ratio is displaced from the outer to the dispersed phase in favor of the outer phase. As a result, the viscosity of the emulsion is less than that of the ternary emulsion.

1.2 Composition of the Outer Oil Phase ($O^2$)

It contains the components that are typical for cosmetic W/O emulsions:
- cosmetic oils in the form of natural or synthetic fatty acid esters, paraffin oils or volatile silicone oils;
- waxes, which are able to form emulsion-stabilizing oleo gels, such as microcrystalline hydrocarbons (micro waxes), beeswax or hydrogenated castor oil (castor wax);
- lipophilic emulsifiers suitable for the preparation of W/O emulsions; pursuant to the invention, these have a polymeric character.

The organosilicon copolymer, a polysiloxane-polycetyl-polyethylene glycol copolymer (EM 90) corresponding to formula II with R=H, has the following subscripts: $n=50$, $m=4$, $o=21$, $p=15$, $x=10$, $y=0$. The derivatized poly(methyl acrylate) $a_1$) (PMAC-W/O) consists of 32 acrylate units, of which 15 are occupied by methyl groups, 15 by oleyl groups and 2 by methoxypolyethylene glycol groups (MW 600).

Reliable W/O emulsifiers, which are, however, not of the invention, are used for comparison: triglycerin trioleate (TGTO), sorbitol mono/dioleate (SMDO), and methylglucose dioleate (MGDO).

1.3 Composition of the O/W Emulsions ($O^1$/W) Functioning as Dispersed Phase These are finely dispersed O/W emulsions, the oil phase ($O^1$) of which consists of vegetable oils, such as soybean or evening primrose oil or conventional, commercial soybean lecithin.

The aqueous phase contains emulsion-stabilizing additives, such as the electrolytes, sodium chloride or magnesium sulfate, and the water-soluble thickeners, sodium polyacrylate (Carbopol 1342) or xanthan gum.

The hydrophilic emulsifiers used are 90% glycerin monostearate made self-emulsifying with potassium stearate (GMS SE), methylglucose mono/distearate (MGMS), polyethylene glycol(60)-castor oil (RZ 60), as well as a hydrophilic, derivatized poly(methyl acrylate) (PMAC-O/W). The latter is based on 32 acrylate units, of which 16 are occupied by methyl groups, 9 by stearyl groups and 7 by methoxypolyethylene glycol groups (MW 600).

1.4 Preparation of Ternary O/W/O and W/O Comparison Emulsions

The components of the outer oil phase ($O^2$), that is, the oil, waxes and emulsifiers, are heated to about 80° C. in order to bring the waxes into solution. Subsequently, the O/W emulsion ($O^1$/W) or the aqueous solution (comparison emulsions), the temperature of which is about 20° C., is incorporated with stirring in accordance with the so-called hot-cold method, for which intensive shearing is required.

1.5 Testing the Stability of the Emulsion

Cosmetic and also pharmaceutical emulsion preparations have to be stable not only at room temperature, but also for several months at 40° C. The required stability at −5° C. can be fulfilled easily; lower temperatures are a problem. Within the scope of the stability tests, the emulsions of some of the experimental series carried out were subjected, in addition, to three freeze-thaw cycles. One cycle consists of a 24-hour storage at −15° C., followed by a 24-hour storage at +20° C.

2. Formulation Examples

2.1 O/W/O Emulsions with Lecithin as Inner Oil Phase ($O^1$)

2.1.1 Aside from the emulsifiers, the outer oil phase contains natural oils and waxes or substances related to these.

As lecithin, a conventional commercial soybean lecithin is used, which is converted by means of an emulsifier (GMS SE) and intensive mechanical processing (rotor-stator homogenizer) at about 60° C. into a very finely dispersed O/W emulsion ($O^1$/W).

As W/O emulsifiers, the organosilicon copolymer EM 90 is used pursuant to the invention and triglycerin trioleate is used for comparison. In the binary reference samples, the lecithin is in the outer oil phase $O^2$.

Result

The emulsions based on the inventive polymeric emulsifier (Examples 1 and 2 as shown in Table 2.1.1), which contain the lecithin in the form of an emulsion in the dispersed phase, are stable. Proof of the ternary structure is provided indirectly by the emulsions (Examples 3 and 4), which contain the lecithin in the external oil phase. Admittedly, these are stable at room temperature and in the cold; however, they break down very rapidly at 40° C. The advantages of the inventive polymeric emulsifier are shown by the ternary comparison emulsions (Examples 5 and 6 as shown in Table 2.1.1), which contain triglycerin trioleate as emulsifier. These comparison emulsions are not stable hot or cold.

2.1.2 The outer oil phase ($O^2$) of the following formulations contains paraffin oil and volatile silicone oil. The emulsifiers are the inventive lipophilic derivatized poly(methyl acrylate) (PMAC-W/O) or, for comparison, methylglucose dioleate.

Result

The inventive polymeric emulsifier forms stable emulsions (Examples 7 and 8 as shown in Table 2.1.2), while the emulsions, produced by means of methylglucose dioleate (Examples 9 and 10) are not stable hot or cold.

2.2 O/W/O Emulsions with a Vegetable Oil as Inner Phase ($O^1$)

2.2.1 The outer oil phase ($O^2$) consists of emulsifier, waxes, paraffin oil and natural or synthetic fatty acid esters. The emulsifiers are the inventive organosilicon copolymer and, in the comparison emulsions, the triglycerin trioleate. As inner phase, a very finely dispersed soybean oil emulsion is used. It contains 1% hydrophilic emulsifier in the form of PEG 60 castor oil. Emulsification is accomplished by the paste method, which corresponds to the principle of mayonnaise manufacture. This has the advantage that only relatively small additions of emulsifier are required. It is characterized in that the oil is stirred into an aqueous emulsifier solution under intensive shear.

The finely dispersed emulsion formed, which has a pasty character because of the high content of a dispersed oil phase (about 80%), is diluted subsequently with water.

Result

The ternary emulsions (Examples 11 to 14 as shown in Table 2.2.1), based on the inventive, lipophilic copolymers, are stable. The ternary structure is confirmed indirectly by the binary comparison emulsions (Examples 15 and 16 as shown in Table 2.2.1), the compositions of which are largely identical with those of Examples 12 and 14, but differ from these in that soybean oil has been added to the outer oil phase (O²). The consequence of this is a clearly lower viscosity and an insufficient stability.

The ternary comparison examples (Examples 17 to 20 as shown in Table 2.2.1), which were prepared with triglycerin trioleate, are stable only at 20° C. and break down when heated or cooled. These examples also clearly show the advantages of the inventive formulations.

2.2.2 The outer oil phase (O²) of the multiple emulsions consists of emulsifier, waxes, paraffin oil or natural or synthetic fatty esters. The inventive organosilicon copolymer is used as W/O emulsifiers and sorbitol sequioleate is used for comparison.

The inner O¹/W phase forms a finely dispersed O/W evening primrose oil emulsion. Hydrophilic, derivatized poly(methyl acrylate) (PMAC-O/W) is used as O/W emulsifier. Emulsification is accomplished at 60° C. by intensive mechanical processing by means of a rotor-stator homogenizer. Before they are processed further to the multiple form, the emulsions are cooled to 20° C. In distinction from the 2.2.1 experimental series, the amount O/W emulsifier is 2% instead of 1%.

Result

The ternary emulsions (Examples 21 to 23 as shown in Table 2.2.2), prepared with the inventive polymeric emulsifier, are stable, while the emulsions, formed with sorbitol mono-dioleate break down at elevated temperatures (Examples 24 and 25 as shown in Table 2.2.2).

| 2.1.1 O/W/O Emulsions, Lecithin | | | | | | |
|---|---|---|---|---|---|---|
| | 1 % | 2 % | 3 % | 4 % | 5 % | 6 % |
| TGTO | — | — | — | — | 3.0 | 3.0 |
| EM 90 | 2.0 | 2.0 | 2.0 | 2.0 | — | — |
| Beeswax | 1.2 | 1.2 | 1.2 | 1.2 | 1.8 | 1.8 |
| Castor Wax | 0.8 | 0.8 | 0.8 | 0.8 | 1.2 | 1.2 |
| Avacado Oil | 12.0 | — | 12.0 | — | 11.0 | — |
| C$_{8/10}$-Triglyceride | 12.0 | — | 12.0 | — | 11.0 | — |
| Jojoba Oil | — | 12.0 | — | 12.0 | — | 11.0 |
| Decyl Oleate | — | 12.0 | — | 12.0 | — | 11.0 |
| Octyl Stearate | — | — | — | — | — | — |
| Soybean Leicithin | — | — | 2.5 | 2.5 | — | — |
| | (28.0) | (28.0) | (30.5) | (30.5) | (28.0) | (28.0) |
| Soybean Lecithin | 2.5 | 2.5 | — | — | 2.5 | 2.5 |

-continued

| | | | | | | |
|---|---|---|---|---|---|---|
| GMS SE | 0.8 | 0.8 | — | — | 0.8 | 0.8 |
| Carbopol 1342 | 0.2 | 0.2 | 0.2 | 0.2 | — | — |
| Xanthan Gum | — | — | — | — | 0.4 | 0.4 |
| Sodium Chloride | 0.5 | 0.5 | 0.5 | 0.5 | — | — |
| Magnesium Sulfate | — | — | — | — | 0.4 | 0.4 |
| Water | 68.0 | 68.0 | 68.8 | 68.8 | 67.9 | 67.9 |
| | (72.0) | (72.0) | (69.5) | (69.5) | (72.0) | (72.0) |

| Stability of the Emulsions | | | | |
|---|---|---|---|---|
| | 1 D/20° C. | 3 M/20° C. | 3 M/40° C. | 3x −15° C. |
| No. 1 | p, s | p, s | p, s | p, s |
| No. 2 | fp, s | fp, s | fp, s | fp, s |
| No. 3 | p, s | p, s | z | p, s |
| No. 4 | fp, s | fp, s | z | p, s |
| No. 5 | p, s | p, s | z | z |
| No. 6 | p, s | p, s | z | z |

Explanation:

| Viscosity/Consistency | Stability |
|---|---|
| p = pasty | s = stable |
| fp = flowable, highly viscous | z = breaks down, oil and/or water separation |
| f = flowable, moderately viscous | |
| (D = day; M = month) | |

| 2.1.2 O/W/O Emulsions, Lecithin | | | | |
|---|---|---|---|---|
| | 7 % | 8 % | 9 % | 10 % |
| MGDO | — | — | 3.0 | 3.0 |
| PMAC-W/O | 2.0 | 2.0 | — | — |
| MicroWax (Mp > 70° C.) | 1.2 | 1.2 | 1.2 | 1.2 |
| Castor Wax | 0.8 | 0.8 | 0.8 | 0.8 |
| Paraffin Oil (30 mPas) | 24.0 | — | 23.0 | — |
| Isohexadecane | — | 12.0 | — | 11.5 |
| Cyclomethylsiloxane(D$_5$) | — | 12.0 | — | 11.5 |
| | (28.0) | (28.0) | (28.0) | (28.0) |
| Soybean Lecithin | 2.5 | 2.5 | 2.5 | 2.5 |
| GMS SE | 0.8 | 0.8 | 0.8 | 0.8 |
| Sodium Chloride | 0.5 | 0.5 | 0.4 | 0.4 |
| Magnesium Sulfate | — | — | — | — |
| Water | 68.2 | 68.2 | 68.3 | 68.3 |
| | (72.0) | (72.0) | (72.0) | (72.0) |

| Stability of the Emulsions | | | | |
|---|---|---|---|---|
| | 1 D/20° C. | 3 M/20° C. | 3 M/40° C. | 3x −15° C. |
| No. 7 | fp, s | fp, s | fp, s | fp, s |
| No. 8 | fp, s | fp, s | fp, s | fp, s |
| No. 9 | p, s | p, s | z | z |
| No. 10 | p, s | p, s | z | z |

| 2.2.1 O/W/O Emulsions, Soybean Oil | | | | | | | | | | |
|---|---|---|---|---|---|---|---|---|---|---|
| | 11 % | 12 % | 13 % | 14 % | 15 % | 16 % | 17 % | 18 % | 19 % | 20 % |
| EM 90 | 2.0 | 2.0 | 2.0 | 2.0 | 2.0 | 2.0 | — | — | — | — |
| TGTO | — | — | — | — | — | — | 4.0 | 4.0 | 4.0 | 4.0 |
| Beeswax | 1.2 | 1.2 | 1.2 | 1.2 | 1.2 | 1.2 | 1.8 | 1.8 | 1.8 | 1.8 |
| Castor Wax | 0.8 | 0.8 | 0.8 | 0.8 | 0.8 | 0.8 | 1.2 | 1.2 | 1.2 | 1.2 |
| Paraffin Oil (30 mPas) | 24.0 | — | — | — | — | — | 21.0 | — | — | — |
| Octyl Stearate | — | 12.0 | — | — | 12.0 | — | — | 10.5 | — | — |
| C$_{8/10}$ Triglyceride | — | 12.0 | 12.0 | — | 12.0 | — | — | 10.5 | 10.5 | — |
| Avacado Oil | — | — | 12.0 | — | — | — | — | — | 10.5 | — |
| Jojoba Oil | — | — | — | 12.0 | — | 12.0 | — | — | — | 10.5 |
| Decyl Oleate | — | — | — | 12.0 | — | 12.0 | — | — | — | 10.5 |
| Soybean Oil | — | — | — | — | 10.0 | 10.0 | — | — | — | — |
| | (28.0) | (28.0) | (28.0) | (28.0) | (38.0) | (38.0) | (28.0) | (28.0) | (28.0) | (28.0) |
| RZ 60 | 1.0 | 1.0 | 1.0 | 1.0 | — | — | 1.0 | 1.0 | 1.0 | 1.0 |
| Soybean Oil | 10.0 | 10.0 | 10.0 | 10.0 | — | — | 10.0 | 10.0 | 10.0 | 10.0 |
| Carbopol 1342 | 0.2 | 0.2 | 0.2 | 0.2 | 0.2 | 0.2 | — | — | — | — |
| Xanthan Gum | — | — | — | — | — | — | 0.5 | 0.5 | 0.5 | 0.5 |
| Sodium Chloride | 0.5 | 0.5 | 0.5 | 0.5 | 0.5 | 0.5 | — | — | — | — |
| Magnesium Sulfate | — | — | — | — | — | — | 0.4 | 0.4 | 0.4 | 0.4 |

-continued

| Water | 60.3 | 60.3 | 60.3 | 60.3 | 61.3 | 61.3 | 60.1 | 60.1 | 60.1 | 60.1 |
|---|---|---|---|---|---|---|---|---|---|---|
|  | (72.0) | (72.0) | (72.0) | (72.0) | (62.0) | (62.0) | (72.0) | (72.0) | (72.0) | (72.0) |

| Stability of the Emulsions | | | |
|---|---|---|---|
|  | 1 D/20° C. | 3 M/20° C. | 3 M/45° C. | 5x −15° C. |
| No. 11 | fp, s | fp, s | fp, s | fp, s |
| No. 12 | fp, s | fp, s | fp, s | fp, s |
| No. 13 | fp, s | fp, s | fp, s | fp, s |
| No. 14 | fp, s | fp, s | fp, s | fp, s |
| No. 15 | f, s | f, s | z | z |
| No. 16 | f, s | f, s | z | z |
| No. 17 | p, s | p, s | z | z |
| No. 18 | p, s | p, s | z | z |
| No. 19 | p, s | p, s | z | z |
| No. 20 | p, s | p, s | z | z |

| 2.2.2 O/W/O Emulsions, Evening Primrose Oil | | | | | |
|---|---|---|---|---|---|
|  | 21 % | 22 % | 23 % | 24 % | 25 % |
| SMDO | — | — | — | 3.0 | 3.0 |
| EM 90 | 2.0 | 2.0 | 2.0 | — | — |
| Beeswax | 1.2 | 1.2 | 1.2 | 1.8 | 1.8 |
| Castor Wax | 0.8 | 0.8 | 0.8 | 1.2 | 1.2 |
| Paraffin Oil (30 mPas) | 24.0 | — | — | 22.0 | — |
| $C_{8/10}$-Triglyceride | — | 12.0 | — | — | — |
| Octyl Stearate | — | 12.0 | — | — | — |
| Jojoba Oil | — | — | 12.0 | — | 11.0 |
| Decyl Oleate | — | — | 12.0 | — | 11.0 |
|  | (28.0) | (28.0) | (28.0) | (28.0) | (28.0) |
| PMAC O/W | 2.0 | 2.0 | 2.0 | 2.0 | 2.0 |
| Evening Primrose Oil | 10.0 | 10.0 | 10.0 | 10.0 | 10.0 |
| Sodium Chloride | 0.5 | 0.5 | 0.5 | — | — |
| Magnesium Sulfate | — | — | — | 0.4 | 0.4 |
| Water | 59.5 | 59.5 | 59.5 | 59.6 | 59.6 |
|  | (72.0) | (72.0) | (72.0) | (72.0) | (72.0) |

| Stability of the Emulsions | | |
|---|---|---|
|  | 1 D/20° C. | 3 M/20° C. | 3 M/40° C. |
| No. 21 | fp, s | fp, s | fp, s |
| No. 22 | p, s | p, s | p, s |
| No. 23 | p, s | p, s | p, s |
| No. 24 | p, s | p, s | z |
| No. 25 | p, s | z | z |

What is claimed is:

1. A liquid or pasty, storage-stable, multiple emulsion of the $O^1/W/O^2$ type, wherein $O^2$ forms an outer phase of the multiple emulsion, a hydrophilic emulsifier being present at the $O^1/W$ interface and a hydrophobic emulsifier being present at the $W/O^2$ interface, further comprising that (1) the hydrophobic emulsifier has an HLB value of at most 8 and is
      $a_1$) a polyacrylate ester with long-chain hydrocarbon and polyoxyalkylene groups, or
      $a_2$) a polyoxyalkylenepolysiloxane with long-chain alkyl groups linked to silicon atoms, and
   (2) the hydrophilic emulsifier is a nonionic emulsifier with an HLB value of more than 8, provided that oily phase $O^1$ is a liquid.

2. The emulsion of claim 1, wherein the hydrophilic emulsifier has an HLB value of more than 12.

3. The emulsion of claims 1 or 2, wherein the hydrophilic emulsifier is
   $b_1$) a partial fatty acid ester of monoglycerin, oligoglycerin or polyglycerin, or
   $b_2$) a polyacrylate ester with long-chain hydrocarbon and polyoxyalkylene groups.

4. The emulsion of claim 3, further comprising that, due to the addition of an alkali salt of a fatty acid, emulsifier $b_1$) is self emulsifying.

5. The emulsion of claim 2, further comprising that the emulsifier $b_1$ is a polyoxyethylene ester of ricinoleic acid.

* * * * *